(12) United States Patent
Selzer et al.

(10) Patent No.: US 10,723,996 B2
(45) Date of Patent: Jul. 28, 2020

(54) RELEASE-MATRICES FOR CONTROLLED RELEASE OF MATERIALS INTO A SURROUNDING MEDIUM

(71) Applicant: KUHNER SHAKER GMBH, Herzogenrath (DE)

(72) Inventors: Sebastian Selzer, Aachen (DE); Daniel Buenger, Moenchengladbach (DE); Iason Zografou, Aachen (DE); Jochen Buechs, Aachen (DE); Doris Klee, Aachen (DE); Barbara Dittrich, Aachen (DE); Markus Jeude, Basel (CH)

(73) Assignee: KUHNER SHAKER GMBH, Herzogenrath (DE)

( * ) Notice: Subject to any disclaimer, the term of this patent is extended or adjusted under 35 U.S.C. 154(b) by 36 days.

(21) Appl. No.: 15/563,422

(22) PCT Filed: Mar. 31, 2015

(86) PCT No.: PCT/EP2015/057111
§ 371 (c)(1),
(2) Date: Sep. 29, 2017

(87) PCT Pub. No.: WO2016/155808
PCT Pub. Date: Oct. 6, 2016

(65) Prior Publication Data
US 2018/0087025 A1    Mar. 29, 2018

(51) Int. Cl.
*C12N 5/00* (2006.01)
*C12M 1/16* (2006.01)

(52) U.S. Cl.
CPC ............ *C12N 5/0068* (2013.01); *C12M 1/16* (2013.01); *C12N 2531/00* (2013.01); *C12N 2533/30* (2013.01)

(58) Field of Classification Search
None
See application file for complete search history.

(56) References Cited

U.S. PATENT DOCUMENTS

| | | |
|---|---|---|
| 2001/0024805 A1 | 9/2001 | Williams et al. |
| 2004/0209361 A1 | 10/2004 | Hemperly et al. |
| 2007/0128246 A1* | 6/2007 | Hossainy .............. A61L 31/10 424/423 |
| 2009/0186411 A1* | 7/2009 | Hoffmann ............. C12M 23/20 435/377 |
| 2012/0093911 A1* | 4/2012 | Malcolm .............. A61K 9/0036 424/433 |
| 2015/0147768 A1* | 5/2015 | Chan .................... C12M 23/12 435/18 |

FOREIGN PATENT DOCUMENTS

| | | |
|---|---|---|
| DE | 10312505 A1 | 9/2004 |
| EP | 1879995 B1 | 4/2012 |
| WO | 2014/047520 A1 | 3/2014 |

OTHER PUBLICATIONS

Fu et al., Expert Opin. Drug Deliv., 7(4):429-444 (2010) (Year: 2010).*
Kajihara et al., J. Control. Rel., 73:271-291 (2001) (Year: 2001).*
Liu et al., Biomater., 26:233-244 (2005) (Year: 2005).*
Maeda et al., J. Control. Rel., 84:15-25 (2002) (Year: 2002).*
Maeda et al., Int. J. Pharma., 261:9-19 (2003) (Year: 2003).*
Zimmermann, EJPB, 59:217-228 (2005) (Year: 2005).*
International Search Report and Written Opinion for International Application No. PCT/EP2015/057111, dated Oct. 27, 2015 (11 pages).
International Preliminary Report on Patentability for International Application No. PCT/EP2015/057111, dated Jul. 18, 2016 (12 pages).
Mari-Kate E. McEntee et al., "Tunable transport of glucose through ionically-crosslinked alginate gels: Effect of alginate and calcium concentration", Journal of applied polymer science, vol. 107, No. 5, Mar. 5, 2008, pp. 2956-2962.
Carelli V. et al, "Evaluation of a silicone based matrix containing a crosslinked polyethylene glycol as a controlled drug delivery system for potential oral application", Journal of controlled release, vol. 33, No. 1, Jan. 1, 1995, pp. 153-162.

* cited by examiner

*Primary Examiner* — Thomas J. Visone
(74) *Attorney, Agent, or Firm* — Kagan Binder, PLLC (57) ABSTRACT

The present invention refers to release matrices which include a material that can be released in a controlled way or with predefined kinetics into a surrounding medium, reaction vessels comprising said release matrices, and release system further comprising a medium which is able to dissolve the embedded material. The present invention further refers to the use of release matrices in several applications and the production method for such matrices. The present invention also relates to a method that al lows control of the release rate of materials from polymer matrices with several factors.

11 Claims, 5 Drawing Sheets

FIG. 1: Schematic view of a reaction vessel comprising a release matrix with embedded material.

FIG. 2: Influence of weight distribution of glucose in a cross-linked polymer system (PDMS) on the glucose release.

FIG. 3: Influence of sterilization on release kinetics of release matrix with 45 weight-% glucose.

FIG. 4: Influence of sterilization on release kinetics of release matrix with 40 weight-% glucose.

FIG. 5: Influence of sterilization on release kinetics of release matrix with 30 weight-% glucose.

RELEASE-MATRICES FOR CONTROLLED RELEASE OF MATERIALS INTO A SURROUNDING MEDIUM

CROSS-REFERENCE TO RELATED APPLICATIONS

This application claims priority to International Application No. PCT/EP2015/057111, filed Mar. 31, 2015, and titled "RELEASE-MATRICES FOR CONTROLLED RELEASE OF MATERIALS INTO A SURROUNDING MEDIUM", which is incorporated herein by reference in its entirety.

FIELD OF THE INVENTION

The present invention refers to release matrices which include a material that can be released in a controlled way or with predetermined kinetics into a surrounding medium, reaction vessels comprising said release matrices, and release system further comprising a medium which is able to dissolve the embedded material. The present invention further refers to the use of release matrices in several applications and the production method for such matrices. The present invention also relates to a method that allows control of the release rate of materials from polymer matrices with several factors.

STATE OF THE ART

Controlled release-matrices are known in the state of the art, for example in DE 103 12 505 A1, wherein a cultivation system for the recovery of particle free pure culture of microorganisms is described. The cultivation system consists of two chambers arranged on top of each other, wherein the lower chamber is a supply chamber which contains nutrient in a solid state and the top chamber is a culture chamber that is a reservoir for particle-free suspensions of organisms. The supply chamber is separated from the culture chamber through a porous physical barrier. The barrier can e.g. be a porous foam with a layer thickness of several millimetres and a pore size of a maximum of about 2 mm. During cultivation of the organisms, the cell material that has died off and particulate metabolism product sink due to gravity into the bottom supply chamber. The particular nutrient substrate is, due to the low pore size of the porous foam, held back in the supply chamber.

US 2001/0024805 discloses microtiterplates containing hydrophilic and hydrophobic areas, wherein nutrients are contained in the coating of the plate. The device allows cultivation and determination of the amount of microorganisms in order to determine the contamination of food by microorganisms.

EP 1879995 B1 discloses a fermentation method with controlled feeding of nutrients into a culture liquid. In order to have the controlled feeding, a diffusion barrier with nutrients embedded therein is used. Exemplary polymers are in particular natural polymers such as alginate, chitosane and polyamide. Also described are silicones and the control of the release rate by using swelling agents.

However, said matrices often have the problem that the release of the included material cannot be efficiently controlled.

Also, the controlled release of liquid materials such as glycerine from polymeric systems is hard to control, as liquid materials tend to flow in an uncontrolled manner through the matrix into the surrounding medium due to their low viscosity.

It is therefore an objective of the present invention to provide release matrices, wherein the release rate can be efficiently controlled. It is a further objective of the present invention to provide release matrices for controlled release of liquid materials.

SHORT DESCRIPTION OF THE INVENTION

The present invention refers to a release-matrix for controlled release of a material C into a medium D, comprising a cross-linked polymer system A based on a polymer B and a material C embedded therein.

In a preferred embodiment, the polymer system A is based on at least a polymer B1, a cross-linking agent B2 and a material C embedded therein.

In another preferred embodiment polymer B1 is a polysiloxane, cross-linking agent B2 is a reactive polysiloxane and material C is a nutrient, pH controlling agent or an inducer.

In another preferred embodiment material C is present in crystalline form, as a powder, or as a liquid. In another preferred embodiment material C is a nutrient or an inducer present in crystalline form, as a powder, or as a liquid. In another preferred embodiment material C is present as a liquid. In another preferred embodiment, material C is a nutrient and is present as a liquid. In another preferred embodiment, the particle size of material C is from 0.1 µm to 2 mm. In another preferred embodiment, material C is a solid (i.e. is in crystalline form or a powder) and has a particle size from 0.1 µm to 2 mm.

The release rate of material C into a medium D is preferably between 0.1-25 g/L*24 h$^{-1}$.

The present invention also refers to a method for controlling the release rate of material from a release-matrix as described above into a surrounding medium D, wherein the release rate is controlled by
  i) the type of polymer B and/or
  ii) an additive added to polymer B, and/or
  iii) the degree of cross-linking of polymer system A, and/or
  iv) the size of particles/drops of material C, and/or
  v) the weight ratio of polymer system A to material C, and/or
  vi) the solubility of material C in medium D, and/or
  vii) the contact surface of polymer system A and medium D, and/or
  viii) the addition of energy into the system, and/or
  ix) the sterilization of the release-matrix.

In a preferred aspect of the invention, the release rate is controlled by all factors i) to ix).

The present invention also refers to a method for producing a release matrix as described above, comprising the steps of:
  i) adding a polymer B, catalyst and optionally a further additive to obtain a mixture 1,
  ii) adding material C to the mixture 1 to obtain mixture 2,
  iii) adding cross-linking agent/cross-linker to mixture 2 to obtain mixture 3,
  iv) polymerising mixture 3.

The present invention further refers to a reaction vessel with one or more cavities comprising a release matrix as described above.

The reaction vessel or the release matrix as described above is preferably packed such that the release matrix is protected from external factors. The reaction vessel or the release matrix is preferably sterilized prior to or after packing. The reaction vessel or the release matrix is thus preferably ready-to-use.

The present invention also refers to a method for producing a reaction vessel comprising a release matrix as described above, comprising the steps of:
i). adding a polymer B, optionally an additive and catalyst to obtain a mixture 1,
ii) adding material C to mixture 1 to obtain mixture 2,
iii) adding cross-linking agent to mixture 2 to obtain mixture 3,
iv) polymerising mixture 3,
v) dispersing the obtained mixture 3,
vi) optionally degasing of the mixture 3,
vii) dosing the obtained polymer system A in step v or vi into a reaction vessel,
vii. hardening mixture 3.

The present invention also refers to a release system, comprising the release matrix or a reaction vessel as described above and further a medium D, which is able to dissolve material C.

The present invention finally refers to the use of a release matrix, a reaction vessel or a reaction system as described above in biosensing, testing of toxicity, growth of microorganisms and/or animal/human cells, or induction or inhibition of protein expression.

DETAILED DESCRIPTION OF THE INVENTION

As described above, it is an objective of the present invention to provide release matrices, wherein the release rate can be efficiently controlled. It is a further objective of the present invention to provide release matrices for controlled release of liquid materials.

This problem is solved by the present release-matrix for controlled release of a material C into a medium D, comprising a cross-linked polymer system A based on a polymer B and a material C embedded therein.

The present invention therefore provides a release-matrix comprising a cross-linked polymer system A based on a polymer B and a material C embedded therein, wherein the release-matrix, when immersed into a medium D, allows controlled release of material C into medium D.

Accordingly, the present invention provides a release-matrix, comprising a cross-linked polymer system A based on a polymer B and a material C embedded therein, wherein the polymer system A allows controlled release of material C into a medium D. Medium D, when added to the release-matrix is able to liberate and take up material C from the polymer system A.

The inventive release-matrix thus comprises a cross-linked polymer system A based on a polymer B and a material C embedded therein, wherein the release-matrix, when immersed into a medium D, allows controlled release of material C into medium D.

The application therefore also provides a release system comprising said release-matrix and a medium D. In this release system, medium D is able to liberate (free) material C from the polymer system A and take up material C or dissolve it.

Polymer System

Polymeric materials that can be used as polymer B are naturally occurring and artificial polymers, in particular the polymers selected from:

Polysaccharides, polysiloxanes, polyacrylic acids, polycarbonates, polyolefins, polycarboxylic acids, polyethers, polyesters, polyamines, polyamides, polysulfones, polyurethanes, polyvinyl based polymers, in particular polyvinyl alcohols, polysiloxanes and copolymers of the listed polymers and derivatives obtained through modification of said polymers or copolymers. Further, microgels and hydrogels that are well known in the art can be used, for example such microgels or hydrogels that are based on polyvinylcaprolactam, polyethyleneglycol, polyvinylalcohol, etc.

From these polymers and copolymers, those containing polysiloxanes are particularly preferred. Polysiloxanes have low toxicity, are thermally stable, do not support microbiological growth, are resistant to chemical and physical influences and have favourable hydrophobic properties. Due to their hydrophobicity, polysiloxanes may preferably be used in release matrices, as they do not tend to dissolve any surrounding medium D, particularly water-based medium. Further, their low toxicity and tendency to not support microbiological growth allows their use e.g. in bacterial growth applications. Thus, polysiloxanes may preferably be used in release matrices, in particular in applications that need the above-mentioned favourable properties.

Polysiloxanes may be selected from the group comprising polyalkylsiloxane, polycycloalkylsiloxane, polyaromaticsiloxane, polyvinylsiloxane, polyhydroxysiloxane, polyacetoxysiloxane, polyhydrosiloxane e.g. polydimethylsiloxane, polydiethylsiloxane, polydiphenylsiloxane, polymethylphenylsiloxane, polyhydroxymethylsiloxane, polymethylhydrosiloxane, and polymethylvinylsiloxane.

Polysiloxanes containing reactive groups, such as hydrogen, vinyl, hydroxy, acetoxy, etc. are particularly preferred. Exemplary reactive polysiloxanes are accordingly polymethylhydrosiloxane, polymethylvinylsiloxane, polymethylhydroxysiloxane, polymethylacetoxysiloxane, etc.

Polyvinylsiloxane (e.g. Polymethylvinylsiloxane) is particularly preferred, as it is a viscous liquid that can be cured (or dried) quickly into a rubber-like solid. This allows to adopt the release-matrix to any surface, such as the wall or bottom of a reaction vessel and cure it thereon in relatively short time.

In some applications, the condensation product of some reactive polysiloxanes may remain in the product and interact with the material C to be released or the surrounding medium D. In some applications, such as controlled growth of bacteria, interaction with such by-products may be unwanted and polyvinylsiloxanes may thus particularly be preferred. In other applications, such as biosensing or testing of toxicity, the condensation product may be of lesser importance and other reactive polysiloxanes such as polyhydrosiloxanes may also be used.

It is also possible to use copolymers of the above-mentioned polymers. For example a polyethyleneglycol-polyvinylsiloxane blockcopolymer or random copolymer may be used. Such a copolymer has the advantage that the hydrophobic-hydrophilic properties and accordingly the release rate of the resulting matrix can be adjusted to the specific application. For example, when a relatively hydrophobic material shall be released into a water-containing medium, it may be preferable to have a polymer matrix with both hydrophobic and hydrophilic properties.

Cross-Linking Agent

In addition to the polymeric material, a cross-linking agent (or cross-linker) is usually used in the release matrix.

Preferred cross-linking agents in the present invention are polyhydrosiloxane (or hydrogen polysiloxanes), such as polymethylhydrosiloxane. Said polymers are preferably used in combination with other materials, as they contain a high amount of reactive Si—H groups and allow a high cross-linking ratio of the resulting polymer matrix.

Thus, in a preferred embodiment of the present invention, polyvinylsiloxanes and polyhydrosiloxanes may be used in combination to form the release matrix.

By varying the cross-linking density of the release matrices, the release rate can be modified. A high cross-linking density will provide a lower release rate, whereas a low cross-linking density will provide a high release rate. Thus, the skilled person can adjust the release rate to the desired rate by modifying the cross-linking rate of the matrices. As described above, this can be done by changing the polymeric material B to cross-linking agent ratio and testing the release rate of the resulting matrices.

Curing and Cross-Linking

Depending on the process, the matrix system can be adjusted to a variation of curing times, e.g: by the use of inhibitors. As material C sometimes tends to sediment in the uncured polymer, a fast curing and cross-linking time is preferred. The curing and cross-linking of the matrix may be catalysed by a highly active platinum complex as catalyst.

Material C

The material C to be released from the polymer system A into the surrounding medium D can be selected according to the needs of the respective application.

Material C may be selected from carbon- or nitrogen-sources such as e.g. glucose, fructose, lactose, galactose, rhamnose, arabinose, glycerine, glycole (e.g. ethyleneglycole), ammonium sulphate, ammonium chloride or urea or complex media such as e.g. yeast extract or inducers such as isopropyl β-D-1-thiogalactopyranoside (IPTG) or pH controlling agents such as e.g. sodium carbonate and solutions containing said materials.

Material C can be present in any form, in particular in crystalline form, as a powder or as a liquid (or fluid).

The size and the particle size distribution of material C (either the solid particle size or the size of liquid drops) can usually be chosen freely. However, in order to have a more defined release rate, the particle size and/or liquid drop size may be selected, or adjusted appropriately. In an embodiment, the particle size of material C is from 0.1 µm to 2 mm. In a preferred embodiment, the particle size is from 0.1-500 µm. In an even more preferred embodiment, the particle size is from about 1 µm to about 200 µm. In another preferred embodiment, the particle size is from about 20 µm to about 200 µm. In an even more preferred embodiment, the particle size is from about 1-20 µm. In another embodiment, particles with defined different particle size distribution or mixtures of two or more fractions with narrow particle size distributions can be used.

It has been found that particle sizes of 20 and 50 µm and in particular bigger particle sizes, a sedimentation process can be observed, such that it is hard to obtain homogeneously distributed material C in the polymer matrix. When finer particles such as those having a particle size lower than 1 µm are used, the electrostatic charge may be high-leading to problems in the handling (in particular dosing) and curing of the polymer system. Thus a particle size from about 1-20 µm is particularly preferred in order to have both low sedimentation and low electrostatic charge.

In order to improve the stability of the dispersion of material C in the polymer B during the manufacturing process, additives may be added. Such additives can for example be polydimethylsiloxanes or polyethyleneglycols or copolymers of both or other materials such as sorbitan laurate and similar materials with poor water solubility.

In case of liquid material C, such as glycerine, it may be hard to keep the material fixed into the matrix and release it in a controlled manner in the surrounding medium, such as water. In such a case, it has been found that a cross-linked polyvinylsiloxane matrix may be preferable, as the liquid can be effectively released in a controlled way into the surrounding medium. To avoid phase separation it is important to control the drop size of material C. Using stabilizing agents or emulsifiers can be beneficial.

The amount of material C in the release matrix can vary in a broad range and may be adopted to the specific application. Material C is usually used in an amount of 1-60 wt.-% based on the weight of the release matrix. In a more preferred embodiment, material C is used in an amount of 10-50 wt.-% in the release matrix. In an even more preferred embodiment, material C is used in an amount of 23-49 wt.-% in the release matrix.

Material C is preferably distributed homogeneously in the polymer matrix A. This may lead to a better control of the release rate and benefits the reproducibility.

Medium D

The choice of medium D depends on the application. Medium D may be selected from liquid fluids, water, water-containing solutions, buffers, organic solvents, alcohols, oils, etc. Medium D may further contain microorganisms.

Control of the Release Rate

The present invention also provides a method for controlling the release rate of a material C from a release-matrix according to the invention into a surrounding medium D.

The release rate of material C from polymer system A into the surrounding medium D may be controlled by a variety of factors, of which some have already been described above.

Accordingly, the release rate may be changed by selecting the type of polymer B. A hydrophopic material such as polydimethylsiloxane may have different release properties than a hydrophilic material such as polyethyleneglycole. Also copolymers, as described above, may be used in order to adjust the hydrophobic-hydrophilic properties and thus the release properties of the resulting release matrix. Such copolymers can be in form of blockcopolymers or random copolymers.

Another way of controlling the release rate may be to add an additive into polymer system A. Such additives can be hydropobic agents such as polydiphenylsiloxanes (PDPS), polydimethylsiloxanes (PDMS), silanes, saturated or unsaturated alkyls, preferably saturated or unsaturated C6-C30 alkyls, even more preferably saturated or unsaturated C10-C18 alkyls, in particular saturated or unsaturated oils, and derivatives thereof, such as the corresponding fluoroalkyls, fluorosiloxanes, fluorosilanes, etc. Additives can also be hydrophilic agents, such as polyethylene glycol (PEG), cellulose, starch, alginate, polysaccharide, etc. additives may be added in order to adjust the hydrophobic-hydrophilic properties and thus the release properties of the resulting release matrix.

Yet another way of controlling the release rate may be by to change the degree of cross-linking of the polymer system A. A way to control the degree of cross-linking is to change the amount of polymer material B to cross-linking agent. A high cross-linking density will provide a lower release rate, whereas a low cross-linking density will provide a high release rate. Thus, the skilled person can adjust the release rate to the desired rate by modifying the cross-linking rate of the matrices. As described above, this can be done by changing the polymeric material B to cross-linking agent ratio and testing the release rate of the resulting matrices.

Yet another way of controlling the release rate may be to change the size of the particle/liquid drops of material C. A larger particle or liquid drop may be released slower and in a non-continuous manner, as not all of the material will have the same access to the surrounding liquid at all the time. As described above, a particle size from about 1-20 μm may be particularly preferred in order to have low sedimentation and low electrostatic charge while having a good release rate.

Yet another way of controlling the release rate may be to change the weight ratio of polymer system A to material C according to the desired release rate. A higher amount of material C in the polymer system may lead to a faster release, whereas a lower amount may lead to a slower release.

Yet another way of controlling the release rate may be the solubility of material C in medium D. The higher the solubility of the material in the surrounding medium, the higher the release rate will be.

Yet another way of controlling the release rate may be polarity of polymer system A, material C and the surrounding medium D. For instance, a polar medium such was water may have a different effect on glucose than an apolar medium such hexane.

Yet another way of controlling the release rate may be to increase or decrease the contact surface of polymer system A and medium D. As described above, the polymer B may be easily adopted to any desired form and then cured into the final polymer system A including material C. Accordingly, polymer system A can be produced in a way to have a large or small surface area, which will later be in contact with a surrounding medium. The higher the contact area with the surrounding medium, the higher the release rate will be.

Yet another way of controlling the release rate may be achieved by adding energy into the system. Energy is usually added to the system via kinetic or thermal energy. For instance, a reaction vessel in which the polymer matrix A together with material C incorporated therein and surrounding medium D may be shaken and/or heated in order to increase the release rate.

Finally, the release rate may be controlled by the sterilization. The irradiation may in particular affect the release within the first 48 h. This influence has to be taken into account during matrix development and/or adaption.

The release rate can also be controlled via the above factors in such a way that a lag-phase is realised. A lag-phase allows the material C to not be immediately released, but after some time after which the polymer system A has been added to medium D. For example, by having a relatively high cross-linking ratio of polymer system A, an immediate release of material C into medium D may be delayed. In another example the addition of a second layer of a polyvinylsiloxane in the magnitude of 0.1 to 5 mm the polymer matrix may delay the release of material C into medium D further.

In another example, a swelling agent may be added to the polymer system A, wherein only swelling processes lead to permeability of the release matrix.

The preferred release rate is between 0.1-25 g/L*24 h$^{-1}$.

Method for Producing Release Matrices

A method for producing a release matrix according to the invention comprises the steps of:
i) adding a polymer B, catalyst and optionally a further additive to obtain a mixture 1,
ii) adding material C to the mixture 1 to obtain mixture 2,
iii) adding cross-linking agent to mixture 2 to obtain mixture 3,
iv) polymerising mixture 3.

It is usually required to mix the mixtures homogeneously prior to polymerisation in order to obtain a homogeneously distributed material C in the polymer matrix.

As described above, the catalyst may preferably be chosen from highly active platinum complexes and the cross-linking agent may be a hydrogen polysiloxane having a high content of reactive Si—H groups that allow cross-linking.

Reaction Vessel Comprising Release Matrices

The release matrices according to the invention may be added into a reaction vessel containing one or more cavities. Preferred reaction vessels are petri dishes, shake flasks and microtiterplates having e.g. 24, 48 or 96 wells.

The material of the reaction vessel can be selected among glass and polymeric materials, in particular polypropylene (PP), polycarbonate (PC), polystyrene (PS), polyamide (PA), polyethyleneterephthalate (PET), polyethylene (PE), etc.

In a preferred embodiment, the release matrix or the reaction vessel comprising the release matrix is packed. The packaging is a functional packaging, which protects the release matrix from external factors such as humidity, pollution or biological contaminants. The packaging has a technical structure that allows protection and sterilization of the packed reaction vessel comprising the release matrix. Packaging can for example be one or several film layers of PE, PET, PE/PET, etc. These film layers close the reaction vessel tight, such that no humidity, pollutants or contaminants can enter the reaction vessel and contaminate the release matrix comprised therein.

In an even more preferred embodiment, the release matrix or the reaction vessel comprising the release matrix is sterilized. Sterilization can be performed by radiation, steam, thermal, gas sterilisation or any other viable sterilization method known to the skilled person. The sterilization process used affects the release matrix and/or the reaction vessel comprising the release matrix and therefore the release rate. For example when using gamma irradiation, the used irradiation power has to be chosen in such a limit/range that the effect of the irradiation is not influencing the practical use or is neglectable or the matrix is adapted prior irradiation (see Experiment 2).

The sterilized release matrix or sterilized reaction vessel comprising the release matrix may be packed before sterilization or immediately after sterilization as described above.

The release matrix or the reaction vessel comprising the release matrix is thus ready-to-use, i.e. it can be sold in its packed and sterilized state and immediately used by the costumer without any other treatment. However, the release matrix or the reaction vessel comprising the release matrix may also be sold without packaging and/or sterilization to the customer who then has to sterilize the product by himself prior to use. For some application, sterilization may not be needed, such that it even can be omitted in such cases.

The costumer may then simply add a medium D, as described above, to the release matrix and use the controlled release of material C for the desired application. Medium D may for instance contain bacteria, yeasts, fungi, plant- or animal cells which grow in a controlled manner when added onto the release matrix.

Method for Producing a Reaction Vessel Comprising the Release Matrix

A method for producing a reaction vessel comprising a release matrix according the present invention comprises the steps of:
i. adding a polymer B, optionally an additive and catalyst to obtain a mixture 1,
ii. adding material C to mixture 1 to obtain mixture 2,
iii. adding cross-linking agent to mixture 2 to obtain mixture 3,
iv. dispersing the obtained mixture 3,
v. optionally degasing of the mixture 3,
vi. dosing the obtained polymer system A in step iv or v into a reaction vessel,
vii. hardening/curing mixture 3.

It is noted that the release matrix can easily be immobilised on either the wall or bottom, or both the walls and the bottom of the reaction vessel. This can either be done by curing the polymer system A directly on the desired portion of the reaction vessel, or first curing the polymer system A and then fixing it on the desired portion. By immobilizing the release matrix in such a way, the release matrix will not float in the surrounding medium (the release matrix is not dispersed in the medium D) and the contact between the medium and the surface of the matrix always remains the same. Accordingly, a constant, defined release rate of material C into medium D is achieved.

Applications Using the Release Matrix or Reaction Vessel Comprising the Release Matrix The release matrix or reaction vessel comprising the release matrix according to the invention may be used in a variety of applications.

Such applications are for example biosensoring, testing of toxicity, growth of microorganisms such as bacteria, yeast, fungi, and induction or inhibition of protein expression. Exemplary microorganisms that can be used in said applications are yeasts (*S. cerevisiae, P. pastoris, H. polymorpha*), funghi, *E. coli*, CHO (Chinese hamster ovaries), etc., but the present invention is not limited thereto.

Accordingly, the release matrix or reaction vessel comprising the release matrix according to the invention can be adopted to any required release material and release rate for the desired application. The skilled person, from the information provided in the present application will be able to adopt the release rate according to the respective application.

Experimental Section

Figure 1:
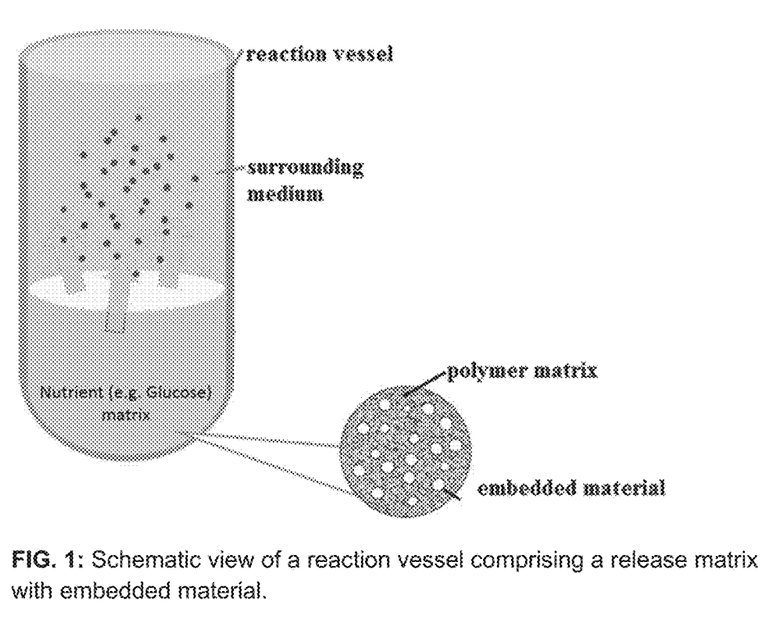
FIG. 1 shows a schematic view of a reaction vessel comprising a release matrix with embedded material.
Figure 2:
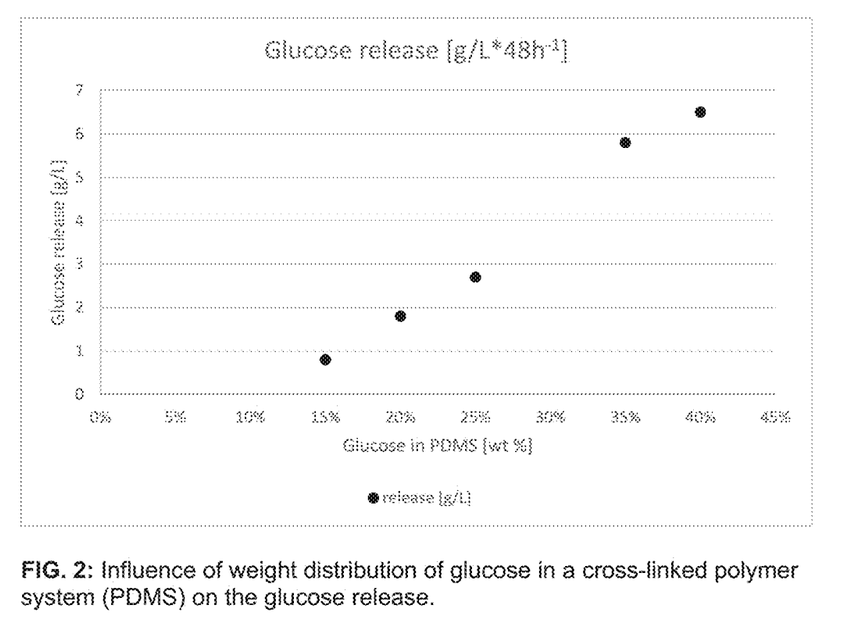
FIG. 2 shows the influence of weight distribution of glucose in a cross-linked polymer system (PDMS) on the glucose release.

Experiment 1:

In the described experiment, the influence of weight distribution of glucose as the release nutrient in a cross-linked polymer system (PDMS) was investigated.

100 g of the polymer system were prepared as following. The amount of the release nutrient embedded within the PDMS system was altered within the ratios of 15-40% [wt].
i) adding 57-81 g of Comp. A (PDMS) to a vessel (stirring bowl),
ii) adding 5.7-8.1 g of Pt-catalyst
iii) adding 15-40 g of glucose,
iv) adding 17.3-24.5 g of the cross-linking agent
v) dispersing the obtained mixture,
vi) degasing of the mixture,
vii) dosing 150 µL of the obtained mixture into the cavities of a reaction vessel (96 well microtiter plate),
viii) hardening/curing the mixture for 20 minutes at 120° C.

The cured plates were incubated at 37° C. for 48 h on an orbital shaker (3 mm Orbit, 1000 rpm). Samples were taken at the end.

The glucose concentration was determined via a total-refractometer. Therefore, 1000 µL sample of medium D were taken from the reaction vessel at defined incubation times (e.g. here after 48 h) and transferred into the refractometer for analysis. The measured values [nD] were compared to a calibration curve, prepared within the expected concentration range.

The results are shown in FIG. 2

Experiment 2:

In a further experiment, the influence of the sterilization process on the release kinetics was investigated.

Figure 3:
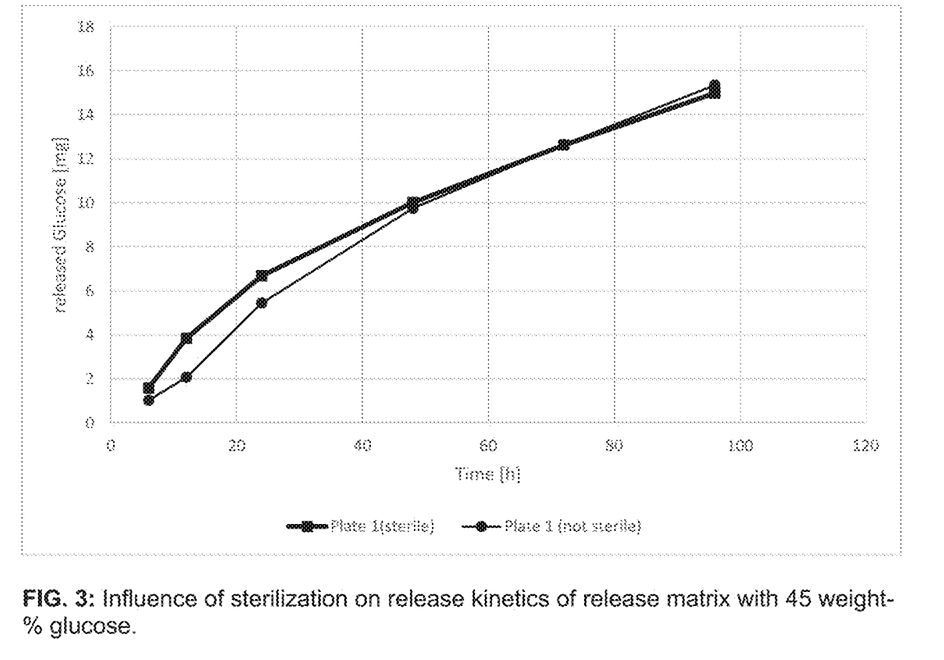
FIGS. 3 to 5 show the influence of sterilization on release kinetics of release matrices with 45, 40 and 30 weight-% glucose.
Figure 4:
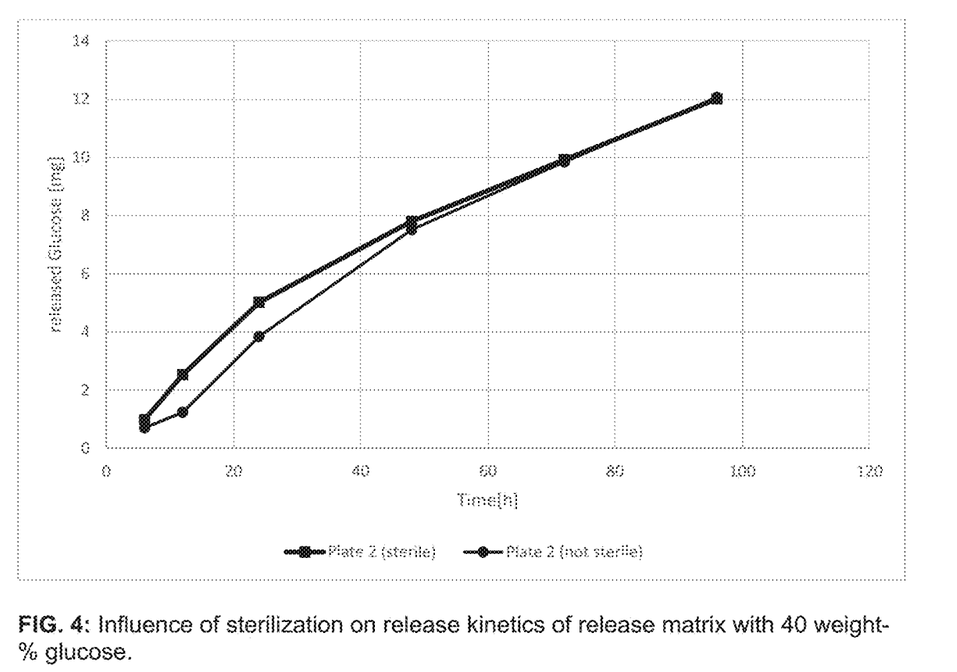
Figure 5:
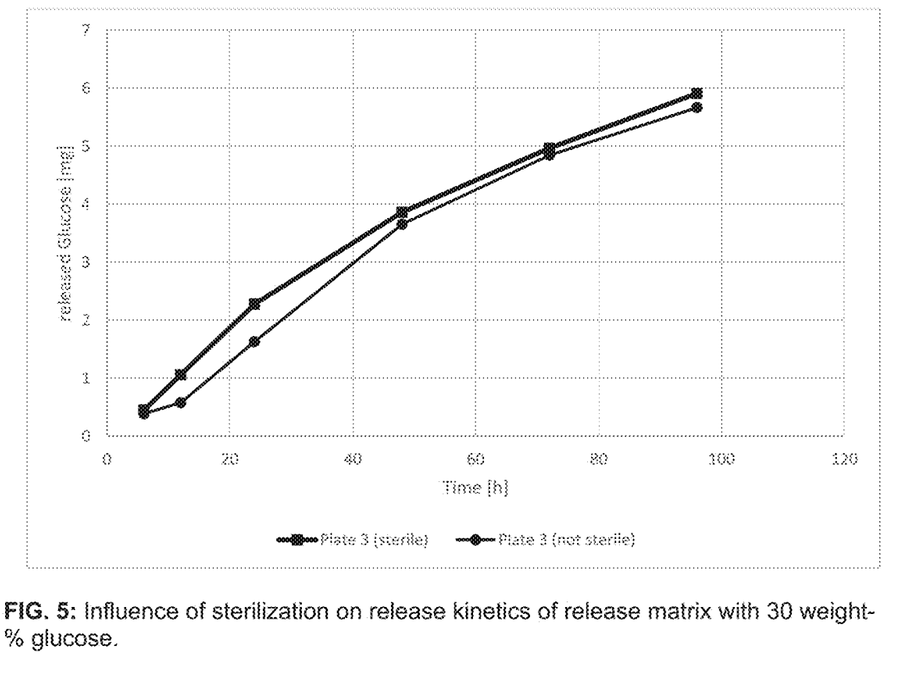

Therefore different samples of release matrices with varying glucose concentration of 45, 40 and 30 weight-% were cultivated (Shaker ISFX-1 from Kühner AG (Switzerland), microtiter plate tablar, 37° C., 1000 rpm, 3 mm Orbit, 96 h) and the glucose release was tested (Total Refractometer, Abbemat 550, Anton Paar GmbH, analytical data (nD) was compared with a predetermined calibration curve).

The graphs in FIGS. 3-5 show the influence of the sterilization process (Gamma irradiation) on the glucose release within the first 48 h. It can be stated that the irradiation affects the release within the first 48 h. This influence has to be taken into account during matrix development and/or adaption.

The invention claimed is:

1. A release-matrix for controlled release of a nutrient, inducer or pH controlling agent into a medium, comprising a cross-linked polymer system formed of a polysiloxane, a reactive polysiloxane, and a nutrient, inducer, or pH controlling agent embedded therein,
   wherein the nutrient, inducer or pH controlling agent have has a particle size of from 1-20 µm, and
   wherein the nutrient, inducer, or pH controlling agent is distributed homogeneously in the release-matrix.

2. The release-matrix according to claim 1, wherein the nutrient, inducer, or pH controlling agent is present in crystalline form or as a powder.

3. The release-matrix according to claim 1, wherein the nutrient, inducer, or pH controlling agent have a release rate into the medium of between 0.1 and 25 g/L*24 h$^{-1}$.

4. A method for controlling the release rate of a nutrient, inducer, or pH controlling agent from a release-matrix according to claim 1 into a surrounding medium, wherein the release rate is controlled by
   i. the type of polysiloxane and/or
   ii. an additive added to the polysiloxane, and/or
   iii. the degree of cross-linking of the polymer system, and/or
   iv. the size of particles/drops of nutrient, inducer, or pH controlling agent, and/or
   v. the weight ratio of the polymer system to nutrient, inducer, or pH controlling agent, and/or
   vi. the solubility of nutrient, inducer or pH controlling agent in the medium, and/or
   vii. the contact surface of the polymer system and the medium, and/or
   viii. the addition of energy into the system, and/or
   ix. the sterilization of the release-matrix.

5. A method for producing a release matrix according to claim 1, comprising the steps of:
   i. adding a polysiloxane, a catalyst, and optionally a further additive to obtain a mixture 1,
   ii. adding a nutrient, inducer, or pH controlling agent to mixture 1 to obtain mixture 2,
   iii. adding a reactive polysiloxane to mixture 2 to obtain mixture 3, and
   iv. polymerizing mixture 3.

6. A reaction vessel with one or more cavities comprising a release matrix according to claim 1.

7. The reaction vessel according to claim 6, which is packed such that the release matrix is protected from external factors.

8. The reaction vessel according to claim 6, which has been sterilized and/or is ready-to-use.

9. A method for producing a reaction vessel comprising a release matrix according to claim 1, comprising the steps of:
   i. adding a polysiloxane, optionally an additive, and catalyst to obtain a mixture 1,
   ii. adding a nutrient, inducer, or pH controlling agent to mixture 1 to obtain mixture 2,
   iii. adding a reactive polysiloxane to mixture 2 to obtain mixture 3,
   iv. dispersing the obtained mixture,
   v. optionally degasing of the mixture,
   vi. dosing the obtained polymer system in step iv or v into a reaction vessel,
   vii. hardening the mixture.

10. A release system, comprising the release matrix according to claim 1, and a medium, which is able to dissolve the nutrient, inducer, or pH controlling agent.

11. A release system, comprising a reaction vessel according to claim 6, and a medium, which is able to dissolve the nutrient, inducer, or pH controlling agent.

\* \* \* \* \*

UNITED STATES PATENT AND TRADEMARK OFFICE
CERTIFICATE OF CORRECTION

PATENT NO. : 10,723,996 B2
APPLICATION NO. : 15/563422
DATED : July 28, 2020
INVENTOR(S) : Sebastian Selzer et al.

Page 1 of 1

It is certified that error appears in the above-identified patent and that said Letters Patent is hereby corrected as shown below:

In the Claims

Claim 1, Line 31, "wherein the nutrient, inducer or pH controlling agent have" should be – wherein the nutrient, inducer or pH controlling agent –

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*